United States Patent
Owen

(10) Patent No.: US 11,617,710 B2
(45) Date of Patent: *Apr. 4, 2023

(54) SELF-EMULSIFYING BIOACTIVE CONCENTRATES

(71) Applicant: Owen Biosciences, Inc., Baton Rouge, LA (US)

(72) Inventor: Donald R. Owen, Baton Rouge, LA (US)

(73) Assignee: Owen Biosciences, Inc., Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/499,534

(22) Filed: Oct. 12, 2021

(65) Prior Publication Data

US 2022/0062140 A1  Mar. 3, 2022

Related U.S. Application Data

(63) Continuation-in-part of application No. 16/052,514, filed on Aug. 1, 2018, now Pat. No. 11,173,103.

(51) Int. Cl.
| | | |
|---|---|---|
| *A61K 8/55* | (2006.01) | |
| *A61K 8/06* | (2006.01) | |
| *A61Q 19/00* | (2006.01) | |
| *A61K 8/67* | (2006.01) | |

(52) U.S. Cl.
CPC ............... *A61K 8/553* (2013.01); *A61K 8/06* (2013.01); *A61K 8/671* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 11,173,103 | B1 * | 11/2021 | Owen | A61K 8/553 |
| 2008/0287393 | A1 * | 11/2008 | Sayo | A61K 8/60 |
| | | | | 514/62 |
| 2013/0095157 | A1 * | 4/2013 | Jeong | A61K 31/07 |
| | | | | 424/49 |

* cited by examiner

*Primary Examiner* — Dominic Lazaro
(74) *Attorney, Agent, or Firm* — Louis C. Paul

(57) ABSTRACT

A self-emulsifying bioactive concentrate produced by a process comprising the steps of (a) creating a lysophospholipid concentrate comprised of a de-oiled lecithin source and 0.1% to 10% of an enzyme with having phospholipase A activity, wherein the lysophospholipid concentrate contains greater than 20% lysophosphatidyl-choline; and (b) combining the lysophospholipid concentrate from step (a) with a retinyl ester formed by the reaction of retinol and one or a mixture of unsaturated fatty acid(s).

20 Claims, No Drawings

SELF-EMULSIFYING BIOACTIVE CONCENTRATES

CROSS-REFERENCE TO RELATED APPLICATIONS

The present application is a continuation in part of co-pending, allowed application Ser. No. 16/052,514, the disclosure of which is incorporated by reference herein.

FIELD OF INVENTION

Self-emulsifying bioactive concentrates that reduce the chronological or environmental skin aging without flaking or peeling of the epidermis, or visible skin redness.

BACKGROUND OF THE INVENTION

Prior art methods for reducing one or more signs of chronological or environmental skin aging achieve thickening of the epidermis via administration of non-conjugated retinoids, conjugated retinol derivatives, conjugated retinoic acid derivatives (collectively retinoids). However, achieving the desired increase in epidermal thickness with retinoids, requires administration at concentrations and/or a dosing regimen that cause one or more deleterious skin effects—typically, increased flaking or peeling of the epidermis, and visible skin redness.

The self-emulsifying bioactive concentrates of the present invention achieve optimized epidermal thickening (and thereby reduce one or more signs of chronological or environmental skin aging) at levels comparable to prior art retinoids, but without (i) negatively impacting skin barrier function; (ii) causing an increase in flaking or peeling; or (iii) visibly increasing skin redness.

SUMMARY OF THE INVENTION

The present invention is directed to a novel bioactive lysophospholipid emulsifiers produced by a process comprising the steps of combining (i) a de-oiled lecithin and (ii) from about 0.1 to about 10% of an enzyme with Phospholipase A ("PLA") Activity; and novel self-emulsifying bioactive concentrates comprised of a bioactive lysophospholipid emulsifier according to the above process and a retinyl ester.

DETAILED DESCRIPTION OF THE INVENTION

In describing component ingredients of the novel bioactive lysophospholipid emulsifiers and self-emulsifying bioactive concentrates comprised of the bioactive lysophospholipid emulsifier, percentages are weight/weight.

"De-oiled lecithin" means crude lecithin from a plant source, preferably soybeans or oilseeds selected from the group of rapeseed, sunflower seed, or maize, that undergoes one or more of filtration, deodorization, fractionation or enzymatic modification to remove triglycerides.

"Phospholipase A Activity" means an enzyme that cleaves a fatty acid moiety on a lecithin moiety, thereby producing a lysophospholipid. An "enzyme with PLA activity" means a phospholipase A1 or phospholipase A2. One preferred, but non-limiting example of an enzyme with PLA2 activity is MAXAPAL® A2 from DSM Food Specialties B.V. (Delft, Netherlands).

"Lecithin" is a complex mixture of phosphatides, consisting chiefly of phosphatidylcholine, phosphatidylethanolamine, phosphatidylserine, and phosphatidylinositol, with varying amounts of triglycerides, fatty acids, and carbohydrates isolated from animal or vegetable sources. In some lecithins, both fatty acids are saturated; others contain only unsaturated acids (for example, oleic, linoleic, or arachidonic acid); and in still others, one fatty acid is saturated, while the other(s) are unsaturated. In most cases, the A2 position is the site of unsaturation.

"Phosphatidylcholine" means 1,2-diacyl-sn-glycero-3-phosphocholines or 3-sn-phosphatidylcholines. Phosphatidylcholines are phospholipids that on hydrolysis yields two fatty acid molecules and one molecule of each of glycerophosphoric acid and choline.

"Lysolecithin" is the product obtained from acid, enzyme or other method of hydrolysis of lecithin. In preferred methods of the present invention, lecithin is partially and selectively hydrolyzed, producing monoacyl phosphatidyl choline (as well as other phosphatides). Phospholipase A1 produces a predominantly unsaturated lysolecithin.

"Lysophosphatidylcholine" is the hydrolysate of phosphatidylcholine obtained by acid, enzyme or other method of hydrolysis, preferably by an enzyme having PLA Activity. It is a monoglycerophospholipid in which a phosphorylcholine moiety occupies a glycerol substitution site. Lysophosphatidylcholine can have different combinations of fatty acids of varying lengths and saturation. The fatty acids are attached at the C-1 (sn-1) position. Fatty acids containing 16, 18 and 20 carbons are the most common.

"Phosphatidic Acid" (diacylglycerol phosphate) is a phospholipid in which one of the primary hydroxyl groups of glycerin is esterified with phosphoric acid; and the two remaining hydroxyl groups (of glycerin) are esterified with long chain, saturated or unsaturated fatty acids.

"Lysophosphatidic acid" ("LPA" also known as mono-acylglycerol phosphate) is a lysoglycerophospholipid. Different combinations of fatty acids of varying lengths and saturation can be attached at the C-1 (sn-1) or C-2 (sn-2) positions. Fatty acids containing 16 and 18 carbons are the most common.

"Oleoyl glyceryl phosphate" ("OGP") can be made by either (i) phosphorylation of a predominantly mono-acyl glyceride (i.e., a glyceride one having a mono-ester content of greater than about 90%) or (ii) reaction of glyceryl phosphate and oleoyl acid chloride. OGP is also referred to in the present application as an "LPA-mimetic" by which is meant OPG contains naturally-occurring LPA or an isomer of LPA.

Retinyl esters are esters of retinol and a fatty acid. Retinoates are esters of retinoic acid and a fatty alcohol or fatty glycerol. Preferred, but non-limiting examples of retinyl esters and retinoates include: Retinyl Linoleate (including Retinyl Safflowerate); Retinyl Oleate; Retinyl Palmitate; Retinyl Palmitoleate; Glyceryl Mono Retinoate; Glyceryl Diretinoate; Oleoyl Glyceryl Retinoate; Diretinyl Succinate; Retinyl Succinic Acid; Acetyl-N-Phenylalanine Retinoate; Retinyl Phosphate; Arginine Retinoate-1; O-Diethyl-N-Aspartyl Retinoate; 0-Diethyl-N-Glutamyl Retinoate; Ascorbyl Retinoate; Hydroxypinacolone Retinoate, Retinyl Retinoate; Tocopheryl Retinoate; and Retinyl Undecenylate.

The bioactive lysophospholipid emulsifiers of the present invention contain greater than about 20% lysophosphatidylcholine.

In certain embodiments, the bioactive lysophospholipid emulsifiers of the present invention may also contain greater than about 10% lysophosphatidic acid and/or an LPA-mimetic.

Preferred, but non-limiting examples of LPA-mimetics include OGP or a cyclic derivative thereof.

An LPA (or LPA-mimetic) may be present at a concentration of from 10 to 50% of the inventive self-emulsifying bioactive concentrates.

The self-emulsifying bioactive concentrates of the present invention are pourable at room temperature, homogenous mixtures at or about room temperature and has no significant visible precipitate.

In certain preferred embodiments, the ratio of lysophosphatidylcholine to retinyl ester in the self-emulsifying bioactive concentrate is about 1:1.

The self-emulsifying bioactive concentrates of present invention can help visibly reduce one or more of "signs of chronological or environmental skin aging" with no, little or reduced visible "deleterious skin effects".

"Signs of chronological or environmental skin aging" means one or more of (i) increases in number, length and/or depth of lines, wrinkles, furrows; (ii) decreased skin elasticity as measured with a ballistometer or ultrasound probe, by histological examination (stained tissue samples from punch biopsies under microscope), or as physically manifested, for example, in sagging; (iii) decreased skin barrier function, expressed as increased trans-epidermal water loss and measured by tape stripping or biomedical devices known in the art including a Tewameter® (Courage+ Khazaka Electronic GmbH, Köln, Germany) and/or histology (degree of differentiation cells or separation of cell layers, for example, separation of the stratum corneum from the underlying stratum lucid um and/or interlamellar separation among the stratum spinosum and stratum granulosum); (iv) decrease in the quantity of collagen fibers and the presence of inflammatory infiltrate; (v) flattening of rete pegs at the dermoepidermal junction. See, e.g., Z. Draelos, "Topical Treatments for Benign Photodamage" in D. Goldberg (ed.), Photodamaged Skin, pp. 146-147 (2004).

Changes in skin redness can be measured by the naked eye of a trained observer, by a chromameter, or in terms of irritation based on changes in level of expression of cytokines and other proteins.

"Deleterious skin effect" means one or more of (a) peeling and/or flaking of the epidermis (b) erythema, upregulation of one or more genes that code for a pro-inflammatory protein, the pro-inflammatory protein gene selected from the group of CASP1, TNF, IL1A, and IL1B, (c) incomplete differentiation of keratinocytes in the stratum granulosum or stratum spinosum, (d) reduced expression of a defensin protein, especially DEFB1, (e) reduced expression of one or more growth factor genes associated with cell turnover and fibroblast crosstalk selected from the group of HBEGF, TGFB1, TGFA, FGF2 and CSF2, and/or (f) reduced expression of one or more genes that code for a corneo-desmosomal protein, including but not limited to DSG2.

The self-emulsifying bioactive concentrate of the invention is preferably used in dermatocosmetic compositions at a concentration of less than about 10%.

In certain preferred embodiments, the self-emulsifying bioactive concentrate of the invention is used in dermatocosmetic compositions at a concentration of less than about 5%.

In daily-use, dermatocosmetic compositions (i.e., applied once daily), the self-emulsifying bioactive concentrate is preferably present at a concentration of less than about 1%, more preferably less than about 0.5%.

In once-weekly, dermatocosmetic compositions (i.e., applied one time over a period of seven consecutive days), the self-emulsifying bioactive concentrate is preferably present at a concentration of less than about 5%, preferably from about 2% to about 5%.

In dermatocosmetic compositions that are oil-in-water (O/W) emulsions, the self-emulsifying bioactive concentrate may be, and preferably is, the primary emulsifier.

In certain dermatocosmetic O/W emulsions, the self-emulsifying bioactive concentrate is the sole emulsifier.

The dermatocosmetic composition may also contain one or more co-emulsifiers (in addition to the self-emulsifying bioactive concentrate).

Preferred, non-limiting co-emulsifiers, include cetyl phosphate, polyglyceryl-3-oleate, polyglyceryl-6-laurate, polyglyceryl-10-oleate, or oleoyl glyceryl citrate.

The self-emulsifying bioactive concentrate may be added to an already-formed emulsion, e.g., after the oil and water phases have been combined, often with heat and mixing. Preferably, the lysophospholipid concentrate is added during a "cool-down" phase.

In dermatocosmetic compositions that are anhydrous, the self-emulsifying bioactive concentrate may be added with or without co-emulsifiers.

The inventive self-emulsifying bioactive concentrate can increase the proliferative properties of a retinyl ester, in particular retinyl linoleate.

In one set of embodiments, the inventive self-emulsifying bioactive concentrate surprisingly and unexpectedly increases the proliferative properties of retinyl linoleate. The prior art teaches the use of dioleoyl phosphatidyl choline (DOPC), also known in the art as the primary component of de-oiled lecithin, to increase the proliferative properties of retinyl linoleate. A first composition—an anhydrous carrier—is prepared comprising (i) retinyl linoleate at a concentration of 1% and (ii) the self-emulsifying bioactive concentrate of the present invention at a concentration of 0.2%. In a second composition comprised of the same anhydrous carrier, retinyl linoleate at a concentration of 1% is combined with DOPC at a concentration of 0.2%. A greater than 50% increase in epidermal thickening is observed in the first composition.

More surprising and unexpected is that the first composition, produces a greater than 200% increase in epidermal thickening.

The first composition—1% retinyl linoleate in combination with 0.2% of the self-emulsifying bioactive concentrate in an anhydrous carrier of the present invention—produces complete differentiation of the skin with observably distinct layers of the epidermis—stratum corneum, stratum lucidum, stratum granulosum, stratum basale. In contrast, the second composition—retinyl linoleate at 1% and DOPC at 0.2% in the same anhydrous carrier—shows a poorly-defined suprabasal layer.

Certain preferred embodiments of the present invention are directed to a dermatocosmetic composition containing (i) the self-emulsifying bioactive concentrate of the present invention and (ii) a retinyl lineolate, preferably retinyl safflowerate, wherein the self-emulsifying bioactive concentrate is present at a concentration of less than 2%, preferably less than 1%, still more preferably less than 0.5%, and the retinyl linoleate is present at a concentration of up to 5%.

In one especially preferred embodiment, the dermatocosmetic composition contains the self-emulsifying bioactive concentrate and retinyl lineolate at a ratio of about 1:5.

In another preferred embodiment, the dermatocosmetic composition contains the self-emulsifying bioactive concentrate, a retinyl ester, preferably retinyl lineolate, and retinol and/or retinal. In this embodiment, retinol and/or retinal is present at a concentration of from about 0.1% to about 1%.

The ratio of retinol to retinyl linoleate may range from 1:2 to 1:6.

In certain embodiments, the self-emulsifying bioactive concentrate is comprised of from 0.1% to 30% of OGP.

In daily-use dermatocosmetic compositions, retinal is preferably present at a concentration of from about 0.1% to 0.5%.

In once-weekly dermatocosmetic compositions, retinal is preferably present at a concentration of from about 0.5% to about 3.5%.

The invention claimed is:

1. A self-emulsifying bioactive concentrate produced by a process comprising the steps of
   (a) providing a lysophospholipid concentrate comprised of a de-oiled lecithin source and 0.1% to 10% of an enzyme having phospholipase A activity, wherein the lysophospholipid concentrate contains greater than 20% lysophosphatidylcholine; and
   (b) combining the lysophospholipid concentrate from step (a) with a retinyl ester formed by the reaction of retinol and one or a mixture of unsaturated fatty acids or a retinoyl ester formed by the reaction of retinoic acid and one or a mixture of unsaturated fatty alcohols.

2. The self-emulsifying bioactive concentrate of claim 1 wherein the retinyl ester or retinyl ester has a melting point below room temperature.

3. The self-emulsifying bioactive concentrate of claim 1 further comprising one or more phosphatides selected from the group of lysophosphatidylethanolamine, lysophosphatidylserine, and lysophosphatidylinositol.

4. The self-emulsifying bioactive concentrate of claim 1 wherein the retinyl ester or a retinoyl ester selected from the group consisting of: retinyl linoleate; retinyl oleate; retinyl palmitate; retinyl palmitoleate; glyceryl mono retinoate; glyceryl diretinoate; oleoyl glyceryl retinoate; diretinyl succinate; retinyl succinic acid; acetyl-n-phenylalanine retinoate; retinyl phosphate; arginine retinoate-1; o-diethyl-n-aspartyl retinoate; o-diethyl-n-glutamyl retinoate; ascorbyl retinoate; hydroxypinacolone retinoate, retinyl retinoate; tocopheryl retinoate; and retinyl undecenylate.

5. The self-emulsifying bioactive concentrate of claim 1 wherein the retinyl ester or retinoyl ester is selected from the group consisting of: retinyl linoleate; retinyl oleate; retinyl palmitate; retinyl palmitoleate; glyceryl mono retinoate; glyceryl diretinoate; oleoyl glyceryl retinoate; diretinyl succinate; retinyl succinic acid; acetyl-n-phenylalanine retinoate; retinyl phosphate; arginine retinoate-1; o-diethyl-n-aspartyl retinoate; o-diethyl-n-glutamyl retinoate; ascorbyl retinoate; hydroxypinacolone retinoate, retinyl retinoate; tocopheryl retinoate; and retinyl undecenylate; and wherein the lysophospholipid concentrate is a pourable, homogenous mixture at or about room temperature.

6. The self-emulsifying bioactive concentrate of claim 1 further comprising an unsaturated fatty acid ester.

7. The self-emulsifying bioactive concentrate of claim 6 wherein the unsaturated fatty acid ester is selected from the group consisting of: ascorbyl linoleate; ascorbyl macadameate; ascorbyl safflowerate; ascorbyl 2 oleate; ascorbyl 3 oleate; ascorbyl 6 oleate.

8. A dermatocosmetic composition comprising the self-emulsifying bioactive concentrate of claim 1.

9. The dermatocosmetic composition of claim 8 comprising the self-emulsifying bioactive concentrate of claim 1 and further comprising lysophosphatidic acid or an LPA-mimetic.

10. The dermatocosmetic composition of claim 8 comprising the self-emulsifying bioactive concentrate of claim 1 furthering comprising an unsaturated fatty acid ester.

11. The dermatocosmetic composition of claim 8 comprising the self-emulsifying bioactive concentrate of claim 7, and further comprising (i) one of lysophosphatidic acid or an LPA-mimetic and ii an unsaturated fatty acid ester.

12. The dermatocosmetic composition of claim 8 further comprising an ethyl unsaturated fatty acid formed by reacting ethanol with a plant-derived triglyceride oil having a content of greater than 80% of: (a) monoene fatty acids; (b) diene fatty acids, or (c) glycerol mono-esters of (a) or (b).

13. The dermatocosmetic composition of claim 12 wherein the source of the plant-derived triglyceride oil is selected from the group consisting of soya, corn, sunflower, walnut, peanut, olive, rapeseed, macadamia, or safflower.

14. The dermatocosmetic composition of claim 8 further comprising a co-emulsifier selected from the group of cetyl phosphate, polyglyceryl-3-oleate, polyglyceryl-6-laurate, polyglyceryl-10-oleate, and oleoyl glyceryl citrate.

15. A self-emulsifying bioactive concentrate produced by a process comprising the steps of
   (a) providing a lysophospholipid concentrate comprised of a de-oiled lecithin source and 0.1% to 10% of an enzyme with having phospholipase A activity, wherein the lysophospholipid concentrate contains greater than 20% lysophosphatidylcholine; and
   (b) combining the lysophospholipid concentrate from step (a) with a retinyl ester formed by the reaction of retinol and one or a mixture of unsaturated fatty acid(s);
   (c) adding lysophosphatidic acid or an LPA-mimetic.

16. The self-emulsifying bioactive concentrate of claim 15 wherein the LPA-mimetic is mono-oleoyl glyceryl phosphate or a cyclic derivative of mono-oleoyl glyceryl phosphate.

17. The self-emulsifying bioactive concentrate of claim 16 wherein lysophosphatidic acid or the LPA-mimetic is present at a concentration of at least 10%.

18. The self-emulsifying bioactive concentrate of claim 16 wherein the retinyl ester is selected from the group consisting of: retinyl linoleate; retinyl oleate; retinyl palmitate; retinyl palmitoleate; glyceryl mono retinoate; glyceryl diretinoate; oleoyl glyceryl retinoate; diretinyl succinate; retinyl succinic acid; acetyl-n-phenylalanine retinoate; retinyl phosphate; arginine retinoate-1; o-diethyl-n-aspartyl retinoate; o-diethyl-n-glutamyl retinoate; ascorbyl retinoate; hydroxypinacolone retinoate, retinyl retinoate; tocopheryl retinoate; and retinyl undecenylate.

19. The self-emulsifying bioactive concentrate of claim 16 further comprising an unsaturated fatty acid ester.

20. The self-emulsifying bioactive concentrate of claim 19 wherein the unsaturated fatty acid ester is selected from the group consisting of: ascorbyl linoleate; ascorbyl macadameate; ascorbyl safflowerate; ascorbyl 2 oleate; ascorbyl 3 oleate; ascorbyl 6 oleate.

* * * * *